(12) United States Patent
Wilson

(10) Patent No.: US 6,511,514 B1
(45) Date of Patent: Jan. 28, 2003

(54) DYNAMIC RESPONSE PROSTHETIC FOOT WITH MULTIAXIAL ANKLE

(76) Inventor: Michael T. Wilson, 3131 Villa La., Missouri City, TX (US) 77459

( * ) Notice: Subject to any disclaimer, the term of this patent is extended or adjusted under 35 U.S.C. 154(b) by 64 days.

(21) Appl. No.: 09/641,011

(22) Filed: Aug. 16, 2000

(51) Int. Cl.⁷ .................................................. A61F 2/66
(52) U.S. Cl. .......................................... 623/49; 623/55
(58) Field of Search ..................... 623/47–56

(56) References Cited

U.S. PATENT DOCUMENTS

| | | |
|---|---|---|
| 4,134,159 A | 1/1979 | Wilson |
| 4,387,472 A | 6/1983 | Wilson |
| 5,116,384 A | 5/1992 | Wilson et al. ................. 623/49 |
| 5,443,527 A | 8/1995 | Wilson |
| 5,482,513 A | 1/1996 | Wilson |
| 5,545,234 A * | 8/1996 | Collier ..................... 623/55 X |
| 5,625,596 A | 4/1997 | Uchida |
| 5,800,570 A * | 9/1998 | Collier ........................ 623/55 |
| 6,165,177 A | 12/2000 | Wilson et al. |

FOREIGN PATENT DOCUMENTS

| | | | | |
|---|---|---|---|---|
| AT | 169349 | * | 11/1951 | ................... 623/55 |
| EP | 0 280 004 A | * | 8/1988 | ................... 623/53 |
| FR | 2 640 499 A | * | 6/1990 | ................... 623/53 |
| RU | 1391643 A | * | 4/1988 | ................... 623/50 |
| RU | 1409258 A | * | 7/1988 | ................... 623/55 |

* cited by examiner

*Primary Examiner*—David H. Willse
(74) *Attorney, Agent, or Firm*—Conley, Rose & Tayon, P. C.

(57) ABSTRACT

A lightweight foot prosthesis is claimed, having a heel, a toe, and a raised instep, an ankle joint incorporated in the foot and capable of motion around each of three perpendicular axes. The foot includes a dorsal member and a plantar member. The prosthesis includes a device for limiting rotation of the ankle joint about at least one of the axes.

20 Claims, 5 Drawing Sheets

US 6,511,514 B1

DYNAMIC RESPONSE PROSTHETIC FOOT WITH MULTIAXIAL ANKLE

TECHNICAL FIELD OF THE INVENTION

The present invention relates generally to a prosthetic foot specifically designed for amputees who require intermediate levels of strength and weight in a prosthesis. More particularly, the present invention relates to construction of a prosthetic foot and ankle joint adapted to provide a desired degree of mobility without excessive bulk.

BACKGROUND OF THE INVENTION

Prosthetic feet are well known in the art, and several such feet have been designed to accomplish one or more objectives.

A useful prosthesis must simulate the operation and motion of an anatomical foot. An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement of the ball of the foot upward and downward, respectively, with respect to the heel that occurs during a normal forward step. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

Known foot prostheses include commercial feet that are capable of all three types of rotation. Typically, however, the prosthetic joints capable of such complicated motion require bulky moving parts and are generally too heavy for some patients, including geriatric or very young patients, or other patients who suffer some degree of muscular weakness.

In addition, it is desirable for a foot prosthesis to be capable of absorbing, storing, and releasing energy. At a minimum, the prosthesis should store enough energy to return itself to a relaxed, unflexed position when the moving force is removed. Prostheses that are designed for use during athletic activities, such as running or playing basketball, are particularly efficient at energy storage and return, providing a springy step. Such energy storage is typically accomplished by the inclusion of coil springs or other reciprocating means that absorb energy on flexure and release it efficiently upon removal of the applied force. The energy-storing components that are typically used for efficient energy return can contribute significantly to the weight of the prosthesis.

In contrast, older, less mobile wearers neither need nor want a high degree of return of stored energy. Instead, it is preferable for the prostheses worn by these wearers to absorb and dissipate a portion of the energy of each flexion. This provides a more stable, cushioned step, and reduces the impact shock experienced by both the wearer and the prosthesis at each step.

Finally, it is necessary that a foot prosthesis be strong enough to support its wearer and durable enough to withstand the stresses of repeated stepping motions over long periods of time. Conventional prostheses tend to be designed for maximized strength, at the cost of added bulk and weight, making them unsuitable for intermediate wearers, who do not subject their prostheses to the same loads as more aggressive wearers, but who need a more robust prosthesis than is typically provided to low-impact users.

Hence it is desired to provide a flexible, durable prosthesis that provides intermediate energy return and a moderately damped step and yet still requires a minimal mass.

SUMMARY OF THE INVENTION

The present invention comprises a foot prosthesis having a lightweight foot portion and an attached lightweight ankle portion capable of a desired degree of rotation around each of three perpendicular axes. As used herein, the words "prosthesis" or "foot prosthesis" refer to both the foot portion of a prosthetic foot and the ankle joint attached thereto.

Simplified construction of the foot and joint mechanism enables the present invention to be at least about 50% lighter than typical foot prostheses. The foot portion includes an integral instep, sole and dorsal member constructed of lightweight polymeric material and is designed to provide support and flexure without excessive weight. The ankle portion includes a pair of ball and socket joints that provides the desired flexibility and stability without excessive mass. Other objects and advantages of the present invention will appear from the following description.

BRIEF DESCRIPTION OF THE DRAWINGS

For a detailed description of a preferred embodiment of the invention, reference will now be made to the accompanying drawings wherein.

DETAILED DESCRIPTION OF THE INVENTION

Figure 1:
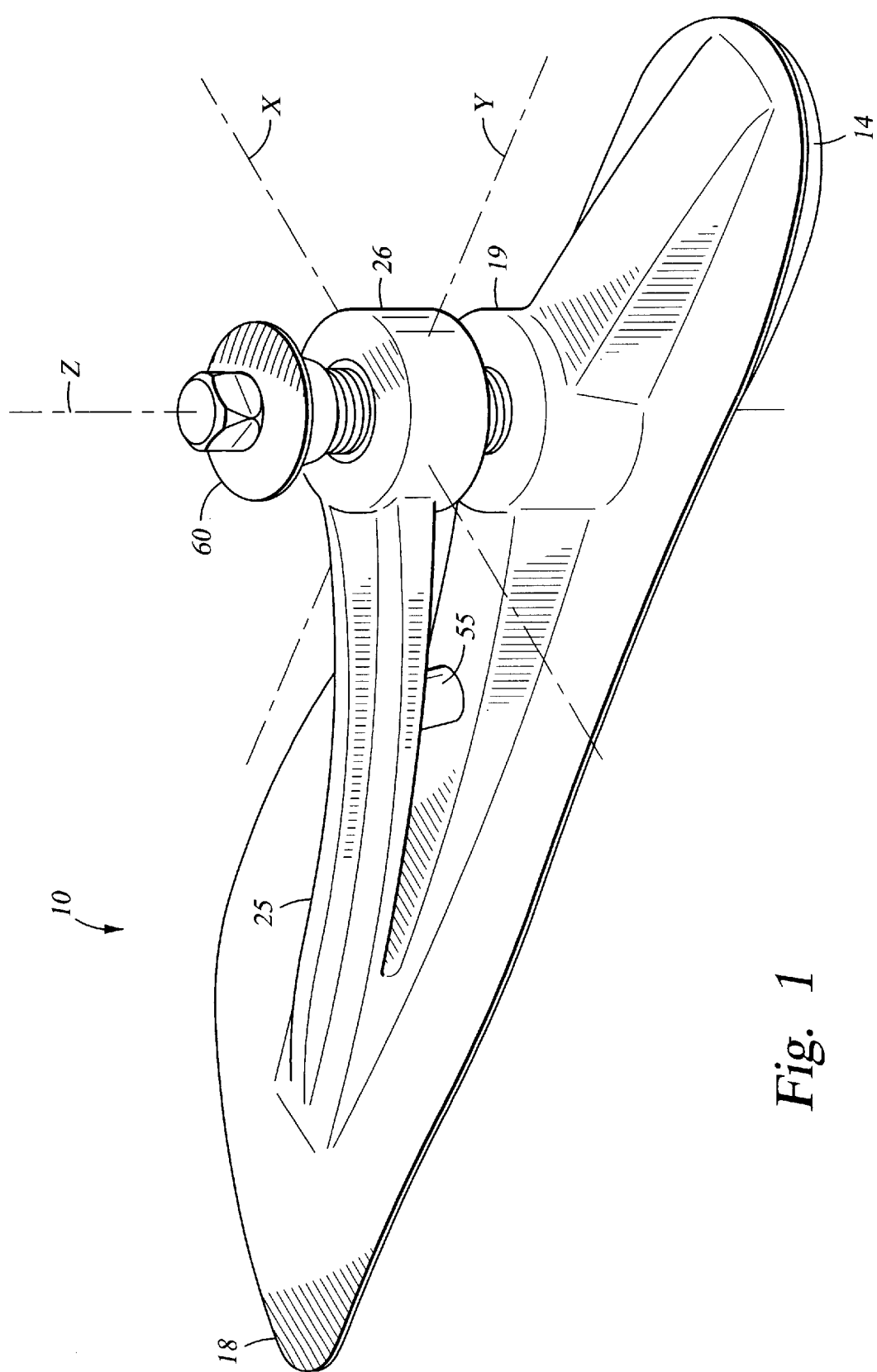
FIG. 1 is a perspective view of the prosthetic foot of the present invention wherein the surrounding cosmesis is shown in phantom.

For purposes of discussion, the x-, y-, and z-axes, about which the foot is designed to rotate, are shown in FIG. 1 and have been assigned as follows. The x-axis is perpendicular to both the leg and foot, passing through the sides of the ankle. The y-axis is perpendicular to the leg and parallel to the foot, and the z-axis is parallel to the leg.

Figure 2:
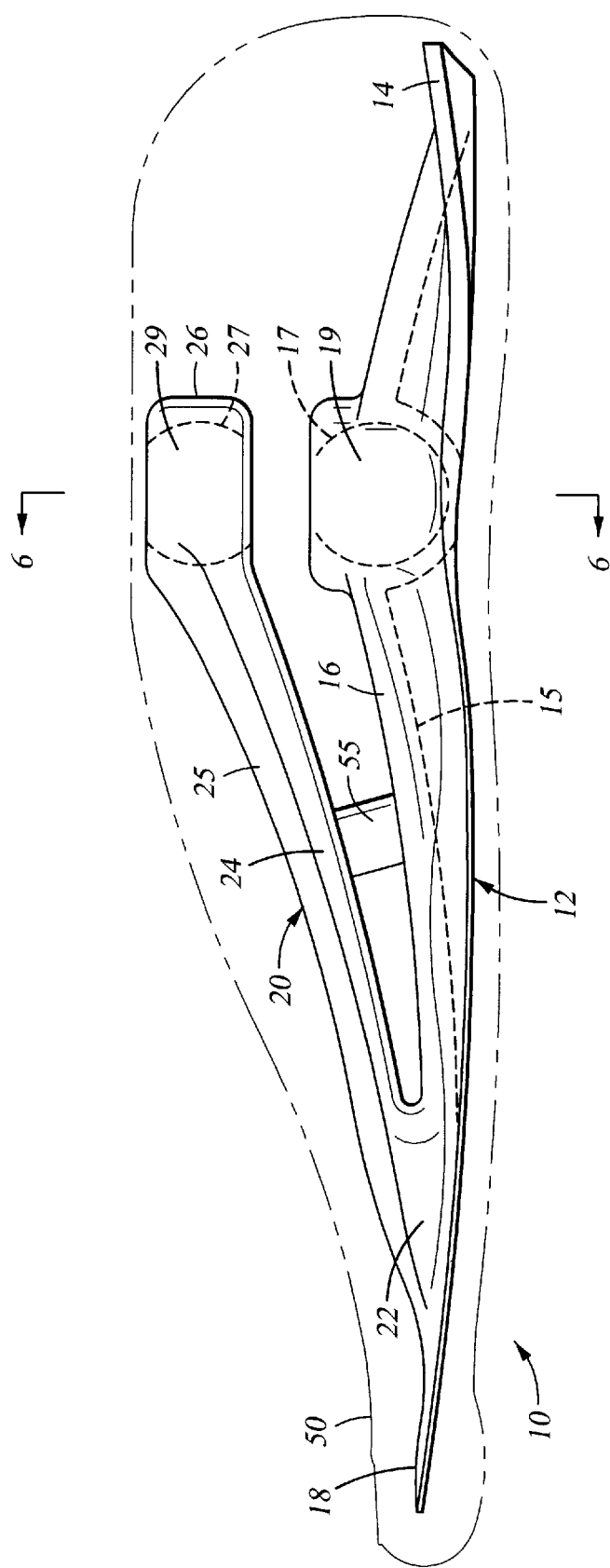
FIG. 2 is a side elevation of the prosthetic foot of FIG. 1.
Figure 3:
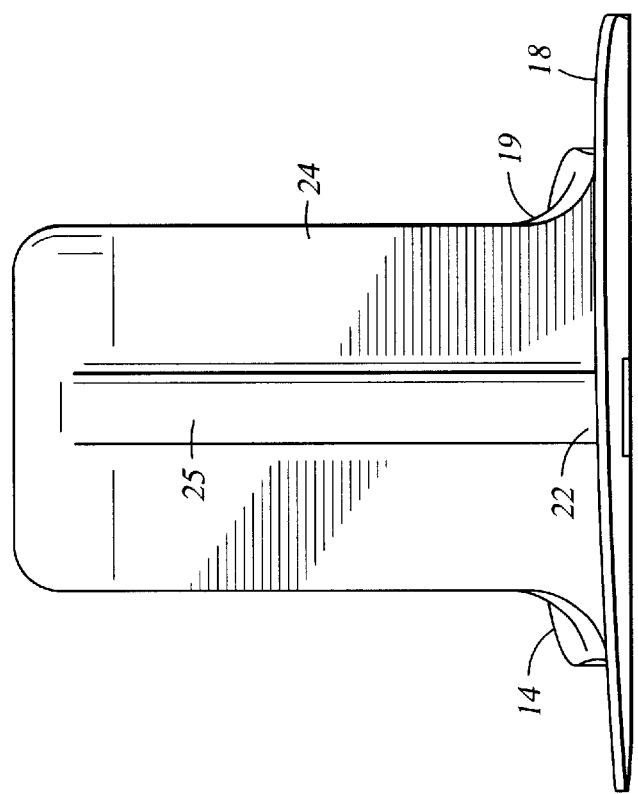
FIG. 3 is a rear elevation of the prosthetic foot of FIG. 1.
Figure 4:
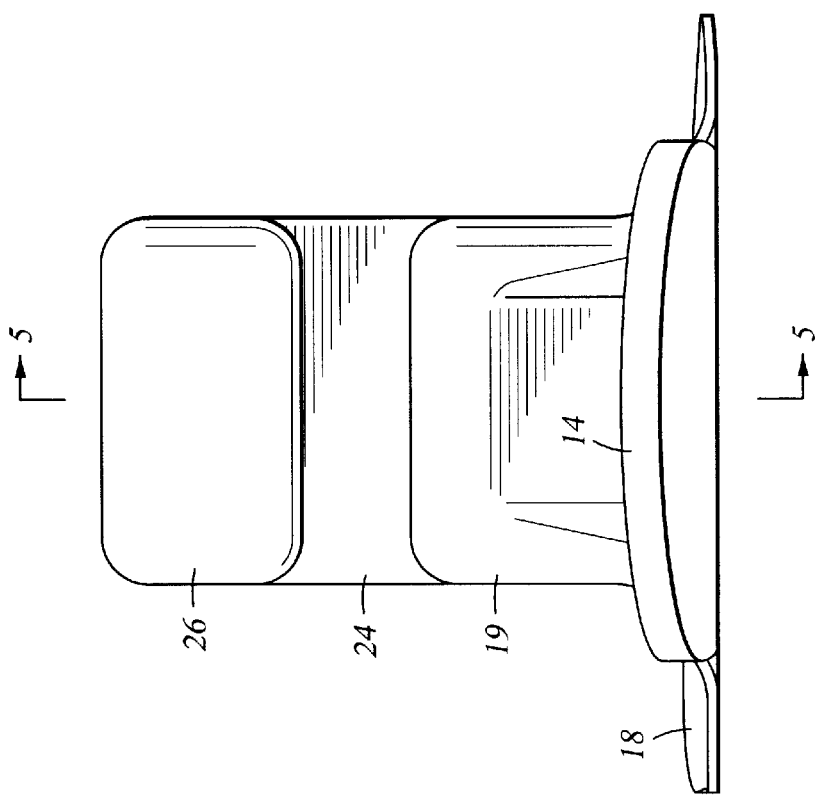
FIG. 4 is a front elevation of the prosthetic foot of FIG. 1.

Referring now to FIGS. 2–4, the prosthetic foot 10 of the present invention includes a plantar member 12 and a dorsal member 20. Plantar member 12 includes a heel 14, a raised instep 16, and a substantially flat toe portion 18, which together form a foot that closely replicates the structure and form of an anatomical foot. Plantar member 12 further includes a lower joint housing 19 at the heel end of instep 16, which includes a lower joint socket 17. Furthermore, it is preferred that instep 16 include a recess 15 (shown in phantom) in its underside. Recess 15 lightens foot 10 without significantly affecting the strength of the prosthesis and also allows the cross-section of the plantar member to be substantially uniform along the middle portion of the foot. This latter advantage is useful when it is desired to form foot 10 by injection molding.

Dorsal member 20 includes a toe end 22, a middle portion 24, and a joint end 26, with an upper joint housing 29 forming an upper joint socket 27 formed at joint end 26. In a preferred embodiment, middle portion 24 includes a reinforcing ridge 25 along its upper, or dorsal, surface. Ridge 25 preferably extends between toe end 22 and joint housing 29. Ridge 25 serves to increase the rigidity of dorsal member 20 and, like recess 15, to allow the cross-section of dorsal member 20 to be substantially uniform along its length. Hence, as dorsal member 20 widens toward toe end 22, the height of ridge 25 decreases proportionally.

Dorsal member 20 is preferably, but not necessarily, integrally or monolithically formed with plantar member 12, i.e. it is preferred that foot 10 be formed from a single piece of material. Foot 10 is preferably constructed of a molded copolymer comprising approximately 90–100% polypropylene and approximately 10–0% polyethylene. It has been found that this copolymer combines heat formability with a desired degree of strength and impact resistance. It has further been found that the addition of black pigment to the polypropylene reduces its brittleness and thus reduces the need for the polyethylene. Other materials having these desired physical properties may be substituted for these polymers without departing from the spirit of the invention. As mentioned above, foot portion 10 may be injection molded. Alternatively, members 12 and 20 can be formed by molding a heated piece of the copolymer in a compression mold having the desired shape.

If dorsal member 20 is not formed integrally with plantar member 12, it is preferred that toe end 22 of dorsal member 20 be rigidly affixed to plantar member 12 such that relative movement between dorsal member 20 and plantar member 12, including rotation, is substantially prevented.

Still referring to FIGS. 2–4, a snubber 55 is positioned between the upper surface of plantar member 12 and the underside of dorsal member 20. Snubber 55 is preferably a compressible cylindrical piece formed from a resilient, elastomeric material, as described in detail below.

FIG. 2 also shows in phantom a cosmesis 50, which is surrounds prosthetic foot 10, such as is known in the art. Cosmesis 50 is preferably constructed of foamed polyethylene and ethylene-vinyl acetate copolymer (EVA). In a preferred embodiment, the inside of cosmesis is formed of expanded polyethylene and the outside is formed of expanded EVA, which provides superior abrasion resistance.

Figure 5:
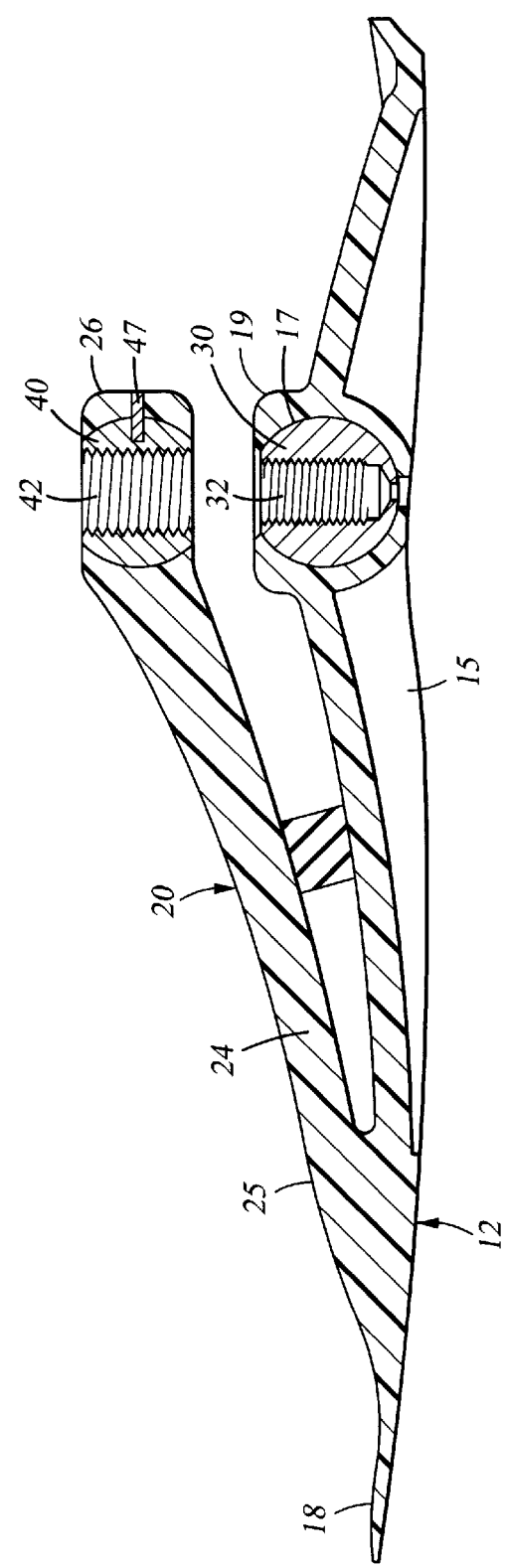
FIG. 5 is a cross section taken along lines 5—5 of FIG. 3.
Figure 6:
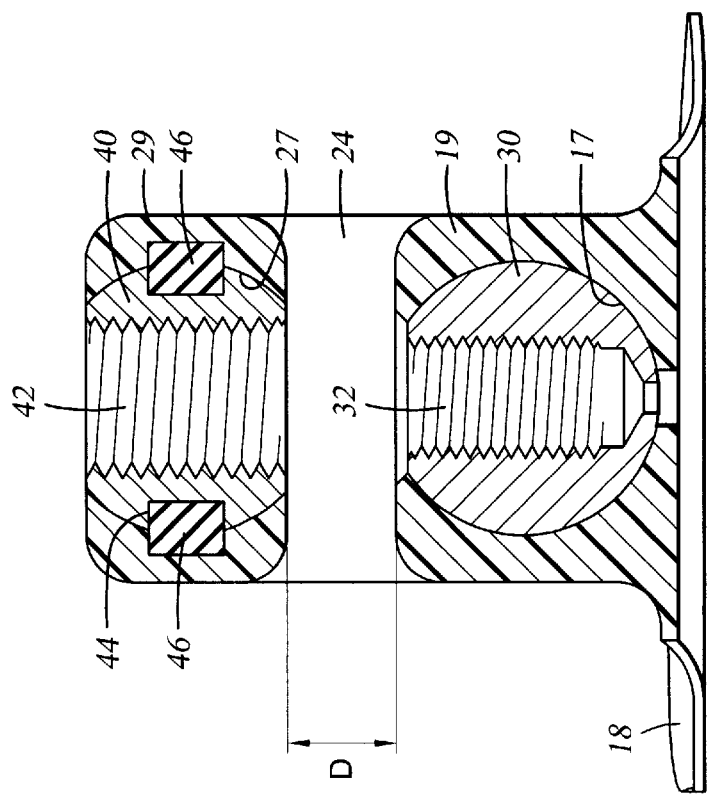
FIG. 6 is a cross section taken along lines 6—6 of FIG. 2.

Referring now to FIGS. 5 and 6, the internal components that make up the joint portion of foot 10 are shown. Lower joint socket 17 houses a lower ball 30 having a vertical threaded bore 32 at least partially therethrough. Similarly, upper joint socket 27 houses an upper ball 40 having a vertical threaded bore 42 therethrough. Dorsal member 20 and plantar member 12 are preferably constructed so that bores 32 and 42 align along a single vertical axis 35. Lower ball 30 and upper ball 40 are each preferably constructed of hardened aluminum alloy, such as 70–75 T6, or hard titanium alloy. Alternatively, lower and upper balls 30, 40 can be formed from stainless steel or other hard metal, but since it is desirable to minimize the weight of the components, it is desirable to avoid using unnecessarily heavy materials such as stainless steel.

Referring now to FIGS. 1 and 6, assembly of foot 10 is completed by threading a connecting spindle 60 (FIG. 1) into the aligned bores 32, 42. Spindle 60 is preferably provided at its upper end with a standard square prosthetic connector, such as an Otto Boch connector or the like. Because spindle 60 is threaded in sequentially from the top of the foot, first into bore 42 and then into bore 32, a desired spacing or gap D (FIG. 6) can be set and maintained between heel end 14 of plantar member 12 and heel end 26 of dorsal member 20. This feature of the invention, along with the rigid connection of toe end 22 of dorsal member 20 to plantar member 12, produces a prosthetic foot that provides certain mechanical improvements over the prior art. This, along with variations in the hardness of snubber 55, allows each prosthetic foot to be customized or adapted to the wearer's activity level and weight as set out in detail below.

It is preferred to provide a set screw or roll pin (not shown), which is threaded through a hole 47 in heel end 26 until it engages spindle 60 and ball 40. The screw is advanced into ball 40 until it no longer engages heel end 26 of dorsal member 20. An example of a suitable size roll pin is 3/32 inch. In this manner, relative movement between spindle 60 and ball 40 is prevented, while leaving upper ball 40 free to rotate within upper socket 27. In some embodiments, lower ball 30 is similarly fixed to spindle 60, while in other embodiments no set screw or roll pin is included in lower ball 30, with the result that ball 30 is free to rotate within lower socket 27, limited only by its engagement with the lower end of spindle 60. Alternatively, epoxy or other adhesive can be used to prevent relative rotation between spindle 60 and either ball 30, 40.

Figure 7:
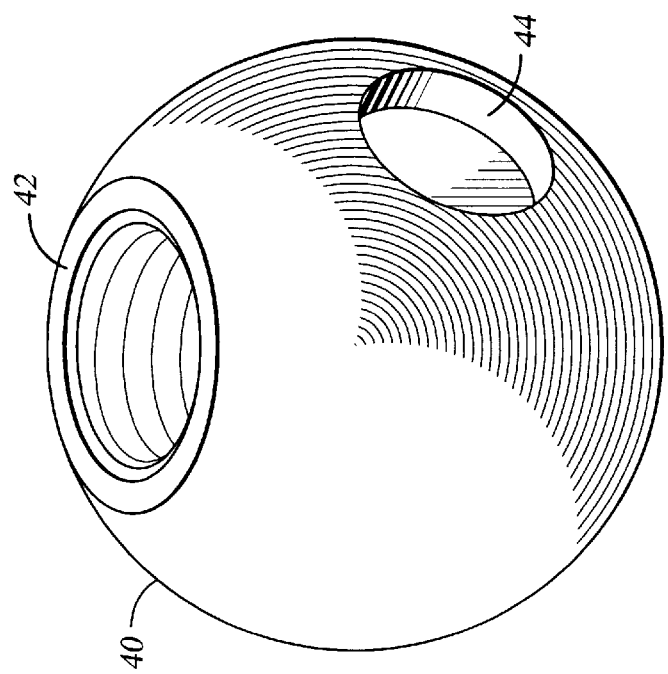
FIG. 7 is an enlarged perspective view of one component of a joint constructed in accordance with the present invention.

Referring now to FIGS. 6 and 7 in particular, it is further preferred to provide each of upper and lower balls 40, 30 with a pair of insets 44, with one inset 44 being on each side of ball 40. According to one embodiment, each inset receives and engages a corresponding elastomeric torque absorber 46 (FIG. 6) that extends outward beyond the surface of the ball. Torque absorbers 46 are placed in insets 44 prior to the molding of the surrounding joint housings 19, 29. Because the material of the joint housings flows around the torque absorbers during molding and conforms to their shape, torque absorbers 46 are held in place by the joint housings. Hence, torque absorbers 46 deform when spindle 60 rotates as a result of torque applied around either the y- or the z-axis. At the same time, when torque is applied to the spindle around the x-axis, both balls 30, 40 can rotate in their respective housings without deforming torque absorbers 46, which can rotate about their respective x-parallel axes. This limitation on, or resistance to, rotation around the y- and z-axes provides advantageous gait management. Torque absorbers 46 preferably comprise 90 durometer urethane or the like.

In another embodiment (not shown), insets 44 are provided in each ball, but torque absorbers 46 are eliminated and the polymeric material of dorsal member 20 and plantar member 12 is allowed to flow into and fill each inset 44 during the molding process. Since the polymeric material, once cured is less resilient than the elastomeric torque absorbers 46, rotation of balls 30, 40 around either the y- or the z-axis is virtually eliminated, which is desirable in certain prosthetic applications.

In still another embodiment, the top ball 40 has insets 44 and torque absorbers 46, but bottom ball 30 has no insets 44 and is smooth except for bore 32. In still another embodiment, the top ball 40 has insets 44 and torque absorbers 46 and bottom ball 30 has insets 44 but no torque absorbers 46. Each of these embodiments produces a different degree of torque resistance and gait management. In each case, torque about the x-axis is resisted, not by the components of the upper and lower joints, but by the mechanics of foot 10 itself. The response of foot 10 to the forces applied during use of the apparatus depends in part in the relative thickness and flexibility of the components of dorsal member 20 and plantar member 12.

Specifically, a preferred embodiment of the prosthetic foot ranges in length from 23 to 30 cm. Dorsal member 20 preferably has a cross-sectional height of 5/16 for a 30 cm foot, and each 1 cm reduction foot length drops the height of dorsal member 20 by 0.022 inch. In addition, it is preferred to provide each size of foot prosthesis in light-, medium- and heavy-duty versions. This is achieved by varying the diameter of snubber 55. For example, it has been found that a snubber comprising 30 durometer silicone, neoprene, or buna-N provides suitable resiliency when provided in 7/8 inch diameter for the firm model, 3/4 inch diameter for the medium duty model, and 5/8 diameter for the light duty model. Although the foregoing values have been found suitable for many users, it may be preferred to use other materials and/or differently sized snubbers, depending on the needs and preferences of the wearer.

Construction

In one embodiment, foot 10 is constructed in a single molding step, using a three-part mold. Lower and upper balls 30, 40 are each positioned in their respective parts of the mold and are each held in place by a screw that engages the mold, or by other suitable means. Heated polypropylene having a volume equal to or slightly larger than the inside volume of the mold is introduced into the mold and assumes the desired shape by injection or compression molding. If desired, the softened plastic can be preformed to approximate the final molded shape before it is placed in the mold. As the polypropylene is introduced into the mold, it deforms around upper and lower balls 30, 40, locking them into place within their respective joint housings 29, 19. Because the preferred polymer has a tendency to shrink slightly upon cooling, it is preferred to encapsulate each ball 30, 40 in a thin layer of silicone or other compressible coating (not shown). Such a layer can be applied by dipping or brushing or any other suitable technique.

As mentioned above, it is important that the toe end 22 of dorsal member 20 be rigidly affixed to plantar member 12. For this reason, it is preferred that both members be formed from a single piece of polypropylene. Alternatively, dorsal member 22 and plantar member 12 can be formed separately and rigidly joined in a subsequent step. This latter embodiment is not preferred, however, because it is believed that this construction would not have the mechanical integrity that a monolithic piece would have.

The distance D between joint end 26 of dorsal member 20 and plantar member 12 is fixed by spindle 60, so relative movement between dorsal member 20 and plantar member 12 is limited to deflection of dorsal member 20 and the corresponding constrained, simultaneous rotation of balls 30, 40 within their respective housings. Preferred values for D range from 13/8 cm for 30 cm to 11/8 cm for 22 cm, although D can be varied from the preferred values.

The rigid attachment of both ends of dorsal member 20 is important because flexure of dorsal member 20 is one of the energy storing mechanisms of the present foot. It has been discovered that if the toe end 22 of dorsal member 20 is not rigidly affixed to plantar member 12, it will buckle in an undesired manner during dorsiflexion, will destabilize the foot, and will not function effectively to return energy during planiflexion. In the present invention, the ends of dorsal member 20 are bent upward, so that dorsal member 20 behaves like a bow and applies a strong returning force. Snubber 55 enhances this desired effect. Further to enhance this effect, it is preferred that the distance between the point where dorsal member 20 connects to plantar member 12 and the center of lower ball 30 is approximately 48% of the overall length of the foot. By lengthening the upper segment, the foot works more smoothly, but this is offset by a reduction in the load capacity of the foot. Further preferred mechanical ratios are as follows. The width of the raised instep at the front (toe end) is preferably 14% of the length of the foot. The thickness of the raised instep where it joins lower housing 29 is 3.4% of the foot length. It is preferred that the instep join the lower housing 29 above center of lower ball 30. It is preferred that spindle 60 have a diameter of 0.5 to 5/8 inch and be tapered by 1/16 from its top end to its bottom end. Finally, it is preferred that dorsal member 20 be predeflected (manufacture to be curved) downward by approximately 1/16 inch downward at a point that is one-third of the way from center of the top ball 40.

It will be understood that the prosthesis of the present invention is capable of rotation about two or more axes simultaneously. Within the mechanical limitations of the two ball joints, rotation of each joint about any one axis has no effect on its rotation about the other two axes. An advantage of the prosthesis of the present invention lies in the fact that it closely simulates the range of motion of an anatomical (natural) foot. Because of insets 44, which are mounted on a line parallel to the x axis, upper ball 40 rotating within upper housing 29 allows a greater degree of flexure about the x axis than is allowed about either the y or z axes. Rotation about both the y and z axes is limited by the compressibility of either torque absorbers 46, or the material of housing 29 that flows into insets 44 during molding. This dissimilarity corresponds to the range of motion allowed by an anatomical ankle.

Several useful discussions of the context and usage of prosthetic feet are given in U.S. Pat. Nos. 5,625,596, 5,482, 513, 5,443,527, 5116,384, which are all incorporated herein in their entireties. For example, the construction of a suitable cosmesis, prosthetic leg attachment, and composition of various components can be derived from those disclosures.

While a preferred embodiment of the invention has been shown and described, modifications thereof can be made by one skilled in the art without departing from the spirit of the invention. For example, the precise shape of the components, the materials of which they are constructed, the degree of movement that is allowed in each direction, and other aspects of the invention can be changed without departing from the spirit of the invention. While the embodiments described above. are preferably constructed of polypropylene because of its lightness, flexibility and resiliency, it will be understood that other materials, and in particular other polymeric materials may be equally suitable. The present prosthesis exploits the tensile strength, and flexibility and manufacturability of polypropylene. The present foot is particularly useful for use at intermediate activity levels, but is robust enough to withstand certain vigorous activities.

What is claimed is:

1. A prosthetic foot, comprising:
   a plantar member having a substantially flat toe end, a raised instep, and a heel end, said plantar member instep including a lower joint housing; and
   a dorsal member having a toe end, a middle portion, and a joint end, said dorsal member joint end including an upper joint housing;
   said dorsal member toe end being rigidly joined to said plantar member between said instep and said toe end;
   wherein said upper and lower joint housings house upper and lower balls, respectively, said upper and lower balls each including a bore.

2. The prosthetic foot according to claim 1 wherein at least one of said upper and lower balls includes a pair of insets.

3. The prosthetic foot according to claim 1 wherein at least one of said upper and lower balls includes a pair of insets and each inset includes an elastomeric member extending out of said inset.

4. A prosthetic foot, comprising:
a plantar member having a substantially flat toe end, a raised instep, and a heel end, said plantar member instep including a lower joint housing;
a dorsal member having a toe end, a middle portion, and a joint end, said dorsal member joint end including an upper joint housing;
said dorsal member toe end being rigidly joined to said plantar member between said instep and said toe end;
said upper and lower joint housings housing upper and lower ball joints, respectively, said upper and lower ball joints each including a bore; and
a rigid shaft received in and engaging said upper and lower bores.

5. The prosthetic foot according to claim 4 wherein the distance between said dorsal member joint end and said plantar member instep is maintained by said shaft.

6. The prosthetic foot according to claim 4 wherein said dorsal member and said plantar member are formed from a single piece of material.

7. The prosthetic foot according to claim 4 wherein said dorsal member and said plantar member are formed separately and said dorsal member toe end is rigidly affixed to said plantar member.

8. The prosthetic foot according to claim 4 wherein said dorsal member middle portion includes a reinforcing rib.

9. The prosthetic foot according to claim 4 wherein said dorsal member has a uniform cross-sectional area between said toe end and said joint end.

10. The prosthetic foot according to claim 4 wherein said upper ball joint is affixed to said shaft so as to prevent relevant movement between said upper ball joint and said shaft.

11. The prosthetic foot according to claim 4 wherein said lower ball joint is affixed to said shaft so as to prevent relevant movement between said lower ball joint and said shaft.

12. A prosthetic foot, comprising:
a plantar member having a substantially flat toe end, a raised instep, a heel end, and a lower joint housing in said instep, said lower joint housing housing a lower ball; and
a dorsal member having a toe end, a middle portion, a joint end, and an upper joint housing in said joint end, said upper joint housing housing an upper ball;
said dorsal member toe end being rigidly joined to said plantar member between said instep and said toe end.

13. The prosthetic foot according to claim 12 wherein at least one of said upper and lower balls includes a pair of insets.

14. The prosthetic foot according to claim 13 wherein at least one of said upper and lower balls includes a pair of insets and each inset includes an elastomeric member extending out of said inset.

15. The prosthetic foot according to claim 12, further including a rigid shaft received in and engaging said upper and lower balls.

16. The prosthetic foot according to claim 15 wherein the distance between said dorsal member joint end and said plantar member instep is maintained by said shaft.

17. The prosthetic foot according to claim 12 wherein said dorsal member and said plantar member are formed from a single piece of material.

18. The prosthetic foot according to claim 12 wherein said dorsal member and said plantar member are formed separately and said dorsal member toe end is rigidly affixed to said plantar member.

19. The prosthetic foot according to claim 12 wherein said dorsal member middle portion includes a reinforcing rib.

20. The prosthetic foot according to claim 12 wherein said dorsal member has a uniform cross-sectional area between said toe end and said joint end.

* * * * *